(12) United States Patent
Reiter et al.

(10) Patent No.: US 12,402,999 B2
(45) Date of Patent: Sep. 2, 2025

(54) APPLICATION DEVICE HAVING A URETERAL CATHETER AND AN INTRODUCTION COMPONENT FOR INTRODUCING THE URETERAL CATHETER, INTRODUCTION COMPONENT AND APPLICATION UNIT

(71) Applicant: UROTECH GMBH, Rohrdorf-Achenmuehle (DE)

(72) Inventors: Niclas Reiter, Holzkirchen (DE); Tobias Hochburger, Rosenheim (DE)

(73) Assignee: UROTECH GMBH, Rohrdorf-Achenmuehle (DE)

( * ) Notice: Subject to any disclaimer, the term of this patent is extended or adjusted under 35 U.S.C. 154(b) by 718 days.

(21) Appl. No.: 17/638,952

(22) PCT Filed: Nov. 26, 2020

(86) PCT No.: PCT/EP2020/083494
§ 371 (c)(1),
(2) Date: Feb. 28, 2022

(87) PCT Pub. No.: WO2021/105278
PCT Pub. Date: Jun. 3, 2021

(65) Prior Publication Data
US 2022/0296356 A1    Sep. 22, 2022

(30) Foreign Application Priority Data
Nov. 27, 2019   (DE) .................... 10 2019 132 160.3

(51) Int. Cl.
*A61F 2/04*      (2013.01)
*A61F 2/966*     (2013.01)

(52) U.S. Cl.
CPC .......... *A61F 2/04* (2013.01); *A61F 2002/048* (2013.01); *A61F 2002/9665* (2013.01); *A61F 2210/009* (2013.01); *A61F 2230/0067* (2013.01)

(58) Field of Classification Search
CPC ........ A61F 2002/048; A61F 2002/9665; A61F 2210/009; A61F 2/82; A61M 27/008
See application file for complete search history.

(56) References Cited

U.S. PATENT DOCUMENTS 4,787,884 A * 11/1988 Goldberg ............ A61M 27/008
                                                        604/164.13
5,647,843 A     7/1997 Mesrobian et al.
(Continued)

FOREIGN PATENT DOCUMENTS

CN    106794334 A    5/2017
CN    109069256 A    12/2018
(Continued)

OTHER PUBLICATIONS

English translation of the International Preliminary Report on Patentability and Written Opinion of the International Searching Authority in PCT/EP2020/083494, mailed May 17, 2022.
(Continued)

*Primary Examiner* — Bruce E Snow
(74) *Attorney, Agent, or Firm* — Collard & Roe, P.C.

(57) ABSTRACT

An application device has a ureteral catheter with a ureteral catheter main body, a receiving body connected to the ureteral catheter main body by means of at least one connection element of the ureteral catheter, and an introduction component for holding the ureteral catheter and for guiding the ureteral catheter through a ureter of a patient along a pliable guide element. The ureteral catheter can be displaced by means of the introduction component in opposite directions of movement along the pliable guide element and the (Continued)

introduction component is designed to guide the ureteral catheter main body and the receiving body during displacement in the respective directions of movement.

19 Claims, 7 Drawing Sheets

(56) References Cited

U.S. PATENT DOCUMENTS

| | | | |
|---|---|---|---|
| 6,258,098 B1* | 7/2001 | Taylor | A61F 2/04 |
| | | | 606/108 |
| 10,226,606 B2* | 3/2019 | Wan | A61F 2/848 |
| 2010/0160848 A1 | 6/2010 | Ostrovsky et al. | |
| 2015/0142127 A1* | 5/2015 | Ponsky | A61M 27/008 |
| | | | 623/23.69 |
| 2015/0182362 A1 | 7/2015 | Taylor et al. | |
| 2017/0156842 A1 | 6/2017 | Isch et al. | |
| 2022/0296356 A1* | 9/2022 | Reiter | A61F 2/94 |

FOREIGN PATENT DOCUMENTS

| | | |
|---|---|---|
| DE | 697 31 027 T2 | 5/2006 |
| DE | 10 2015 001 505 A1 | 8/2016 |
| EP | 2977075 A1 | 1/2016 |

OTHER PUBLICATIONS

First Office Action in CN 202080078247.9, dated Dec. 21, 2023 with English Translation.

International Search Report of PCT/EP2020/083494, mailed Mar. 3, 2021.

* cited by examiner

APPLICATION DEVICE HAVING A URETERAL CATHETER AND AN INTRODUCTION COMPONENT FOR INTRODUCING THE URETERAL CATHETER, INTRODUCTION COMPONENT AND APPLICATION UNIT

CROSS REFERENCE TO RELATED APPLICATIONS

This application is the National Stage of PCT/EP2020/083494 filed on Nov. 26, 2020, which claims priority under 35 U.S.C. § 119 of German Application No. 10 2019 132 160.3 filed on Nov. 27, 2019, the disclosure of which is incorporated by reference. The international application under PCT article 21(2) was not published in English.

The invention relates to an application device with a ureteral stent, which comprises a ureteral stent main body and a receiving body connected to the ureteral stent main body by means of at least one connection element of the ureteral stent, and with an introduction component for holding the ureteral stent and for guiding the ureteral stent through a ureter of a patient along a pliable guide element. Further aspects of the invention relate to an introduction component for such an application device as well as to an application unit.

For inserting ureteral stents, a guide wire is often introduced into a kidney of a patient via a urethra, a bladder and a ureter. Subsequently, the ureteral stent can be placed with the aid of an introduction aid via the guide wire. After positioning the ureteral stent, the introduction aid as well as the guide wire is removed. Extracting the guide wire usually results in a shape change, mostly a rolling up movement, at a distal end or at both ends of the ureteral stent. This shape change prevents unwanted sliding out of the ureteral stent and thus serves for fixing it in the urinary system of the patient.

In order to avoid a cystoscopy for removing the ureteral stent, the latter can include a magnet at the distal end thereof, which can be magnetically connected to a catheter, in particular Tiemann catheter, which comprises an end attracting the magnet. A magnetic force acting between the magnet and the attracting end of the catheter is sufficient to remove the ureteral stent coupled to the catheter via the magnet based on the catheter in shortest time.

From DE 697 31 027 T2, a stent for implantation in a ureter between a urinary bladder and a kidney for preventing reflow of urine into the kidney is known. The stent comprises an elongated tubular body with a urinary bladder end section and a kidney end section, liquid paths in the kidney end section and over at least a part of the tubular body, means at the kidney end section and at the urinary bladder end section for curvature of the ends of the stent such that they are held in the renal pelvis and in the urinary bladder, and means for suppressing the flow of urine from the urinary bladder to the kidney via the stent. The stent includes either no passage or a passage in the urinary bladder end section, which is closed after the implantation of the stent, wherein the urinary bladder end section constitutes the suppressing means.

DE 10 2015 001 505 A1 describes a device, which approximately looks like a urinary catheter from the outside, but which is composed of a sheath hose part and a tip part, which is arranged at the bladder-side end of the sheath hose part via a guide wire centrally located in the sheath hose part such that the tip part is translationally extendable from the sheath hose part and twistable in relation to the sheath hose part by actuation of the guide wire at the grip element, such that the tip part, in its extended working position, exposes a grip part fixed to the guide wire with elastically deformable grip arms, wherein the latter ones capture and wind up pull threads or thread loops upon twisting the grip part, which are externally arranged at the distal end area of the double J ureteral stent.

It is the object of the present invention to provide an application device, an introduction component as well as an application unit of the initially mentioned type, by means of which a simplified alignment of a ureteral stent upon introduction thereof towards a kidney can be effected.

This object is solved by the subject matters of the independent claims. Advantageous developments of the invention are disclosed by the features of the dependent claims, the following description as well as the figures.

A first aspect of the invention relates to an application device with a ureteral stent, which comprises a ureteral stent main body and a receiving body connected to the ureteral stent main body by means of at least one connection element of the ureteral stent, as well as with an introduction component for holding the ureteral stent and for guiding the ureteral stent through a ureter of a patient along a pliable guide element.

According to the invention, it is provided that the ureteral stent is displaceable in directions of movement opposite to each other along the pliable guide element by means of the introduction component and the introduction component is formed to guide the ureteral stent main body and the receiving body upon displacing in the respective directions of movement. This is advantageous since the ureteral stent and thereby the ureteral stent main body as well as the receiving body can thus be commonly displaced in relation to the pliable guide element and in the directions of movement opposite to each other based on the introduction component such that a particularly accurate orientation and thereby alignment of the ureteral stent upon the introduction thereof towards the kidney of the patient is allowed. Upon displacing in the respective opposite directions of movement, advancing and retracting the ureteral stent in the urethra, the bladder, the ureter or the kidney can accordingly be effected by means of the introduction component.

The ureteral stent can also be referred to as ureter stent. The ureteral stent main body can also be referred to as stent, thus medical implant for keeping vessels or hollow organs open. The introduction component can also be referred as a so-called "pusher". The guide element can preferably be formed as a guide wire, thus as a wire for guiding the application device. Principally, a configuration of the guide element as a plastic wire or plastic pipe is also conceivable. The guide element can be introduced into the kidney of a patient via a urethra, a bladder and the ureter. The ureteral stent can then also be introduced into the kidney and thereby passed through the ureter along the guide element together with the introduction component. The ureteral stent can be held on the introduction component via the pliable guide element, wherein the pliable guide element can hereto be passed both through the ureteral stent and through the introduction component.

Particularly preferably, the introduction component can be formed to hold the ureteral stent main body and the receiving body spaced from each other, in particular at a constant distance to each other, independently of the displacement in the directions of movement opposite to each other. Thereby, a possible collision as well as for example a tilt of the receiving body in relation to the ureteral stent main body resulting therefrom in introducing towards the kidney can advantageously be avoided, whereby complications in introducing the ureteral stent can be avoided. In other words, a possible relative movement between the ureteral stent main body and the receiving body in displacing can thus be avoided.

The introduction component, which can also be referred to as introduction aid, can preferably be integrally formed, whereby a particularly simple operability of the introduction component can be achieved. Thereby, additional mechanics for detaching the introduction component from the ureteral stent after intended placement thereof in the urinary system is in particular not required.

In an advantageous development of the invention, the receiving body has ferromagnetic characteristics. In other words, the receiving body can thus be formed as a ferromagnet at least in certain areas. Thereby, the receiving body can be attracted by a magnet, which can for example be received on a catheter, in particular Tiemann catheter, or be part of the catheter. Alternatively thereto, the receiving body can also be formed as a magnet body at least in certain areas and thereby be magnetic itself. Both the magnetic attractability and the configuration as a magnet facilitate the removal of the ureteral stent, especially as the receiving body can then be fast connected to the catheter (Tiemann catheter) and removed, in particular extracted, from the urinary system—as a result of correspondingly acting magnetic forces.

In a further advantageous development of the invention, the ureteral stent main body is rotatable together with the receiving body in relation to the pliable guide element based on the introduction component. This is advantageous since the orientation and thereby the alignment of the ureteral stent can hereby be further improved in the introduction thereof. In particular, the introduction component can be formed to hold the ureteral stent main body and the receiving body such that they are rotatable in synchronous manner, thus in other words without rotational offset, based on the introduction component.

In a further advantageous development of the invention, the at least one connection element is non-rigidly or pliably formed. This is advantageous since the receiving body can be particularly easily pulled towards a catheter, in particular Tiemann catheter, upon later removal of the ureteral stent, wherein the connection element can therein be deformed with particularly low force effort, whereby a magnetic connection between the receiving body and the catheter can be established in simplified manner.

In a further advantageous development of the invention, the at least one connection element is strained by means of the introduction component with the ureteral stent held on the introduction component. This is advantageous since the ureteral stent thus is particularly captively held on the introduction component. Thus, it can be particularly advantageously provided that the introduction component is clamped between the receiving body and the ureteral stent main body in certain areas via the connection element, whereby an unintended detachment of the ureteral stent from the introduction component can be particularly advantageously prevented. In other words, thus, the connection element can be held under mechanical strain via the introduction component if the ureteral stent is held on the introduction component.

In a further advantageous development of the invention, the at least one connection element is formed as a thread element or as a wire element. This is advantageous since the connection element thereby requires particularly little space and thereby does not unnecessarily aggravate the introduction of the ureteral stent towards the kidney. Moreover, a particularly simple deformation of the connection element is possible by the configuration of the connection element as a thread element or wire element such that the connection element does not impede a magnetic coupling between the receiving body and a catheter for removing the ureteral stent.

In a further advantageous development of the invention, the introduction component comprises a recess for introducing and holding the receiving body.

This is advantageous since the receiving body can be arranged in the recess in particularly space-saving manner and a possible, undesired dropping out of the receiving body can additionally be avoided in simple manner by means of the recess. Therein, the recess can quasi form a receptacle for the receiving body.

In a further advantageous development of the invention, the introduction component comprises at least two pipe sections, into which the pliable guide element can be introduced, as well as at least one connection area connecting the at least two pipe sections to each other, wherein the at least two pipe sections and the at least one connection area delimit the recess. This is advantageous since the introduction component thus has an outer contour, by which the introduction component is suitable for introduction into respective channels of the urinary system such as for example the urethra or the ureter to particular extent. By the possibility of introducing the pliable guide element into the pipe sections, the introduction component can be particularly captively introduced along the pliable guide element and for example into the bladder of the patient to cite just one example. The pipe sections can comprise respective pipe passage openings, through which the pliable guide element can be passed.

In a further advantageous development of the invention, a first pipe section of the at least two pipe sections is formed as a proximal end of the introduction component, into which a distal main body end of the ureteral stent main body facing the receiving body is introduced at least in certain areas at least with the ureteral stent held on the introduction component. This is advantageous since a particularly captive, detachable attachment of the distal main body end and thereby of the ureteral stent main body to the introduction component is given by the introduction of the distal main body end. The distal main body end can also be referred to as distal end of the ureteral stent main body. Thus, the distal main body end and the proximal end of the introduction component (pusher) can overall be in contact with each other with the ureteral stent held on the introduction component.

Therein, the end respectively located closer to the body center is understood as the proximal end of the respective element of the application device, the element of the application device respectively farther away from the body center is understood as the distal end.

In a further advantageous development of the invention, the distal main body end introduced at least in certain areas can be held on the first pipe section in an introduction position by means of the guide element with the ureteral stent held on the introduction component, wherein the distal main body end is formed to autonomously deform from the introduction position into a basic position of the distal main body end with the guide element detached from the ureteral stent main body and to thereby move out of the first pipe section. Thus, the guide element can hold the distal main body end in the introduction position. This is advantageous since the distal main body end in the introduction position thereof can for example be introduced into the urethra particularly low in resistance and can deform without further auxiliary means and thereby quasi in autonomous manner from the introduction position into the basic position if the guide element is detached from the ureteral stent main body, thus for example is pulled out of the ureteral stent main body and thereby separated, in particular spaced, from the ureteral stent main body. As a result of the deformation from the introduction position into the basic position, the distal main body end can autonomously move out of the first pipe section. In other words, the guide element can thus hold the distal main body end introduced at least in certain areas in the introduction position with the ureteral stent held on the introduction component, wherein the distal main body end is formed to autonomously deform from the introduction position into the basic position with the guide element detached from the ureteral stent main body and thereby move out of the first pipe section.

In the basic position, the distal main body end can preferably have a larger radial extension than in the introduction position. Thereby, undesired sliding out or slipping of the ureteral stent main body, for example passed through the ureter, in the basic position thereof can be avoided. The ureteral stent main body can be correspondingly safely held in the ureter. In contrast to the introduction position, the distal main body end can preferably be coiled in the basic position. The same can also apply to a proximal main body end of the ureteral stent main body opposing the distal main body end. In other words, it can be provided that the proximal main body end opposing the distal main body end can also autonomously deform from the introduction position thereof into the basic position thereof. Preferably, the proximal main body end can also be coiled in the basic position thereof. In particular, the two main body ends of the ureteral stent main body opposing each other can each be j-shaped coiled in the respective basic position thereof. In the respective introduction position thereof, the main body ends opposing each other can each be stretched and pre-strained compared to the basic position. In summary, the distal main body end and/or the proximal main body end can deform from the introduction position into the basic position by detaching the guide element from the ureteral stent main body. By means of the guide element, the distal main body end and/or the proximal main body end can be held pre-strained in the introduction position. In summary, the distal main body end and/or the proximal main body end can preferably coil upon deforming from the introduction position into the basic position.

In a further advantageous development of the invention, the distal main body end is formed, upon movement thereof out the first pipe section and by deforming from the introduction position into the basic position, to extract the receiving body from the recess via the at least one connection element. This is advantageous since the receiving body can thus be detached from the introduction component without further auxiliary means by deforming the distal main body end and via the connection element. Upon movement out of the first pipe section, the distal main body end, during deformation thereof from the introduction position into the basic position, can support itself on the first pipe section and thereby move the receiving body out of the recess via the at least one connection element.

In particular, the pliable guide element can first be pulled at least out of the first pipe section, whereby the distal main body end can deform from the introduction position into the basic position and can thereby autonomously move out of the first pipe section. Thereby, the distal main body end can support itself on the first pipe section and therein extract the receiving body from the recess via the connection element. Thus, the distal main body end can automatically move out of the first pipe section by the deformation from the introduction state into the basic state.

In further advantageous embodiments of the application device according to the invention, the first, proximal pipe section of the introduction component can have a constriction in a proximal end area, wherein an internal diameter of the constriction is smaller than an external diameter of the distal end of the ureteral stent main body. There is also the possibility that the first, proximal pipe section of the introduction component is formed tapering in a proximal end area such that the internal diameter of the constriction is smaller than the external diameter of the distal end of the ureteral stent main body. Thereby, it is ensured according to the invention that the distal end of the ureteral stent main body cannot or cannot excessively penetrate into the introduction component. Thereby, it can be reliably prevented that difficulties in detaching the two elements from each other occur.

In further advantageous embodiments of the application device according to the invention, the first, proximal pipe section of the introduction component can comprise a first pipe passage opening, the diameter of which decreases towards the receiving body such that it is approximately equal to or equal to a diameter of a passage opening of the receiving body. However, there is also the possibility that a tube is arranged in the first, proximal pipe section of the introduction component, wherein the tube comprises a tube passage opening, the diameter of which decreases towards the receiving body such that it is approximately equal to or equal to a diameter of a passage opening of the receiving body. Furthermore, there is the possibility that the tube comprises a tube passage opening, the diameter of which is approximately equal to or equal to a diameter of a passage opening of the receiving body. The mentioned embodiments ensure a secure and easy passage and movability of the guide element within the passage openings of the ureteral stent main body, of the introduction component and of the receiving body. By the corresponding adaptation of the diameters, it can be reliably prevented that the guide element can for example encounter the front face of the receiving body and thus prevents further pushing the guide element through the introduction component and the receiving body.

In further advantageous embodiments of the application device according to the invention, the recess in the introduction component can comprise at least one inclination and/or at least one step in the end area facing the first pipe section such that a diameter of the recess increases in the area of the inclination or step.

The mentioned inclination or step can also be formed by a distal end area of the tube arranged in the first, proximal pipe section of the introduction component. The formation of such an inclination or step facilitates sliding of the receiving body out of the recess in case of extraction of the guide element from the ureteral stent main body, the introduction component and the receiving body.

In a further advantageous embodiment of the application device according to the invention, at least one notch or peripheral recess for receiving and guiding the connection element is formed in a proximal end area of the first, proximal pipe section of the introduction component. For example, the ends of a thread- or wire-shaped connection element are combined and at least partially held in the notch. By such a construction, it is advantageously prevented that the ureteral stent and the distal end of the ureteral stent main body, respectively, can unintentionally detach from the proximal end of the introduction component.

In a further advantageous embodiment of the application device according to the invention, a proximal end area of the first, proximal pipe section of the introduction component is formed funnel-shaped for receiving the distal main body end. There is also the possibility that the funnel shape is formed by a proximal end area of the tube arranged in the first, proximal pipe section of the introduction component. The funnel shape facilitates docking as well as retaining the distal ureteral stent main body on the proximal end of the introduction component.

In a further advantageous embodiment of the invention, the at least one connection area is deformable between a release position, in which the at least two pipe sections are tilted in relation to each other by means of the at least one connection area and thereby the recess is expanded at least in certain areas for releasing the receiving body, and a holding position, in which the recess is constricted compared to the release position for holding the receiving body. This is advantageous since a simplified sliding of the receiving body out of the recess is thus allowed by the deformation of the connection area from the holding position into the release position. Thus, while the receiving body can be captively held in the recess in the holding position, the receiving body can be passed out of the recess in particularly simple manner in the release position. As a result of the deformation of the connection area from the holding position into the release position, respective central axes of the pipe sections can tilt to each other and thereby form an angle with each other. In the non-tilted state, the respective central axes of the pipe sections can be oriented parallel or coaxially to each other. The at least one connection area can in particular be elastically deformable between the holding position and the release position.

In a further advantageous development of the invention, the at least one connection area can be held in the holding position based on the guide element with the ureteral stent held by means of the introduction component as well as with the guide element introduced into the at least two pipe sections, wherein an elastic deformation of the at least one connection area from the holding position thereof into the release position thereof can be blocked by means of the introduced guide element. This is advantageous since the elastic deformation of the connection area from the holding position thereof into the release position thereof can accordingly be effected solely by detaching the guide element from the introduction component. Accordingly, by detaching the guide element from the introduction component, the detachment of the ureteral stent, thus of the ureteral stent main body and the receiving body, from the introduction component can also be assisted at the same time.

Thus, the at least one connection area can for example be applied with a mechanical pre-strain in the holding position based on the pliable guide element. By passing the pliable guide element out of the first pipe section, the mechanical pre-strain can be cancelled, whereby the connection area can autonomously and elastically deform from the holding position into the release position.

The introduced guide element can thus prevent the elastic deformation of the connection area from the holding position thereof into the release position thereof. Accordingly, the introduced guide element can hold the connection area strained in the holding position thereof.

In a further advantageous embodiment of the application device according to the invention, the connection element is at least partially guided on an outer surface of the proximal end of the introduction component with the ureteral stent held on the introduction component. Advantageously, such an arrangement of the connection element can be constructively simply produced.

In a further advantageous embodiment of the application device according to the invention, it comprises a mounting sleeve, wherein the mounting sleeve is formed such that an internal diameter of the mounting sleeve is equal to or larger than an external diameter of the introduction component. Such a mounting sleeve serves for fixing the receiving body in the recess of the introduction component. In particular before passing the guide element through the corresponding passage openings of the introduction component and the receiving body, the receiving body can thus be securely held and fixed in the recess, respectively.

A second aspect of the invention relates to an introduction component for an application device according to the first aspect of the invention. The features presented in context of the inventive application device according to the first aspect of the invention as well as the advantages thereof correspondingly apply to the inventive introduction component according to the second aspect of the invention and vice versa.

A third aspect of the invention relates to an application unit, which comprises an application device according to the first aspect of the invention as well as the pliable guide element, on which the ureteral stent as well as the introduction component are received. The features presented in context of the inventive application device according to the first aspect of the invention and the inventive introduction component according to the second aspect of the invention as well as the advantages thereof correspondingly apply to the inventive application unit according to the third aspect of the invention and vice versa. The pliable guide element can in particular be passed through respective passage openings of the ureteral stent main body and of the receiving body as well as through the introduction component.

Further features of the invention are apparent from the claims, the embodiments as well as based on the drawings. The features and feature combinations mentioned above in the description as well as the features and feature combinations mentioned below in the embodiments are usable not only in the respectively specified combination but also in other combinations without departing from the scope of the invention.

There shows.

In the following figures, identical reference characters relate to identical or comparable features of the various embodiments of the application device 10.

Figure 1:
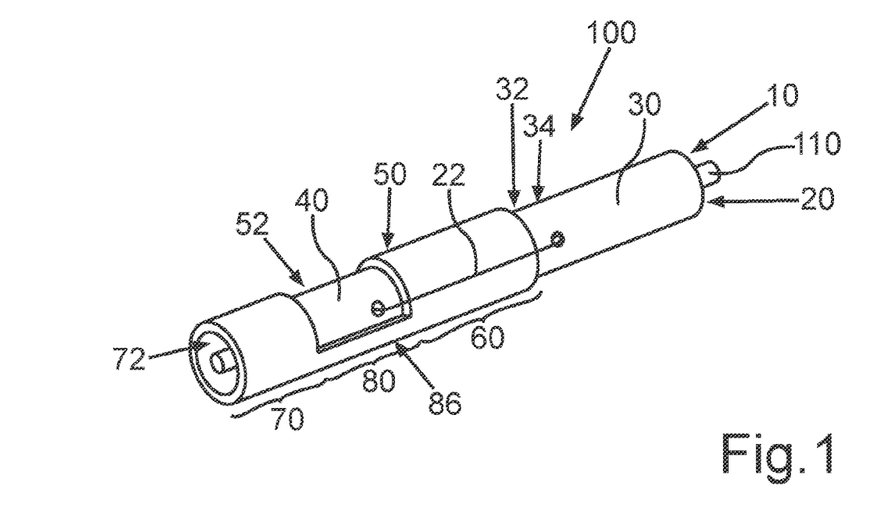
FIG. 1 a schematic perspective view of an application unit, which comprises an application device and a pliable guide element, at which a ureteral stent as well as an introduction component of the application device are displaceable in guided manner.
Figure 2:
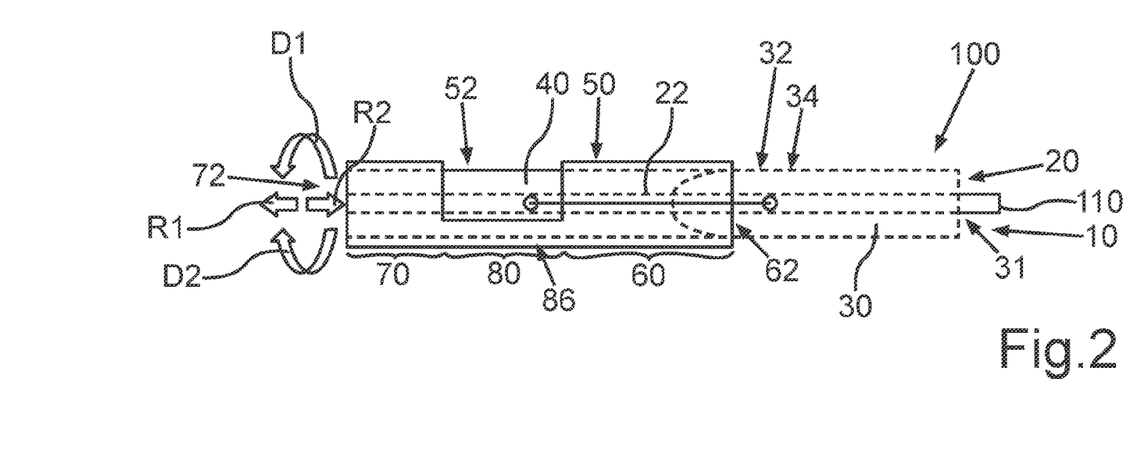
FIG. 2 a schematic side view of the application unit, wherein directions of movement opposite to each other are shown, along which the ureteral stent is displaceable in translational manner and in relation to the pliable guide element based on the introduction component, and wherein rotational directions opposite to each other are shown, in which the ureteral stent is rotatable in relation to the pliable guide element based on the introduction component.

FIG. 1 and FIG. 2 each show various views of an application unit 100, which comprises an application device 10 as well as a pliable guide element 110. A ureteral stent 20 on the one hand and an introduction component 50 of the application device 10 on the other hand can be arranged on the pliable guide element 110, which can for example be formed as a guide wire.

The ureteral stent 20 comprises a ureteral stent main body 30 and a receiving body 40 connected to the ureteral stent main body 30 by means of at least one connection element 22 of the ureteral stent 20. The at least one connection element 22 is presently non-rigidly or pliably formed and configured as a thread element. However, an alternative configuration of the connection element 22 as a wire element is also conceivable. One recognizes that the connection element 22 is at least partially guided on an outer surface of a proximal end of the introduction component 50 with the ureteral stent 20 held on the introduction component 50.

Figure 3A:
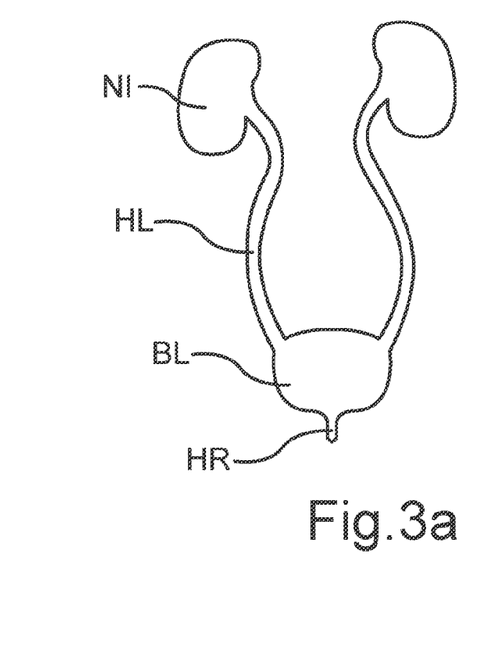
FIG. 3a-e respectively schematic top views to a urinary system of a patient, based on which the introduction of the pliable guide element towards a kidney of the urinary system, a subsequent placement of the ureteral stent via the guide element by means of the introduction component, the removal of the guide element and of the introduction component as well as a desired position of the ureteral stent in the intended use thereof are apparent.

The introduction component 50 of the application device 10 serves for holding the ureteral stent 20 and for guiding the ureteral stent 20 for example through a ureter HL of a urinary system of a patient recognizable in FIG. 3a to FIG. 3e along the pliable guide element 110. In FIG. 3a, the urinary system is schematically illustrated without the application unit 100 and without the application device 10, respectively, and comprises a urethra HR, a bladder BL, ureters HL and kidneys NI.

Figure 3B:
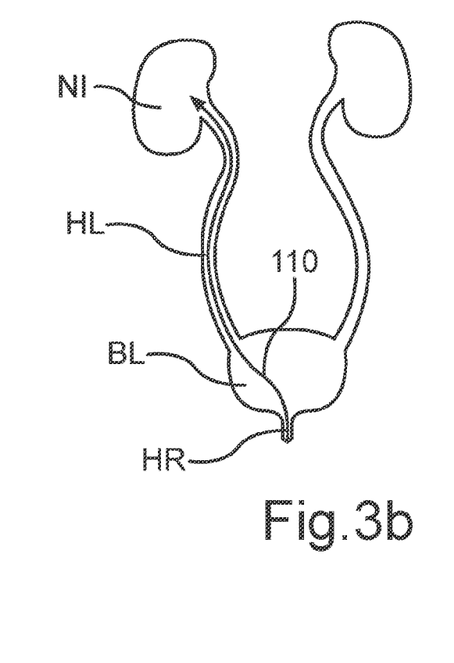

In order to insert the ureteral stent 20 into the urinary system, the pliable guide element 110 (here: guide wire) can first be introduced into one of the kidneys NI via the urethra HR, the bladder BL and one of the ureters HL as is apparent based on FIG. 3b.

Figure 3C:
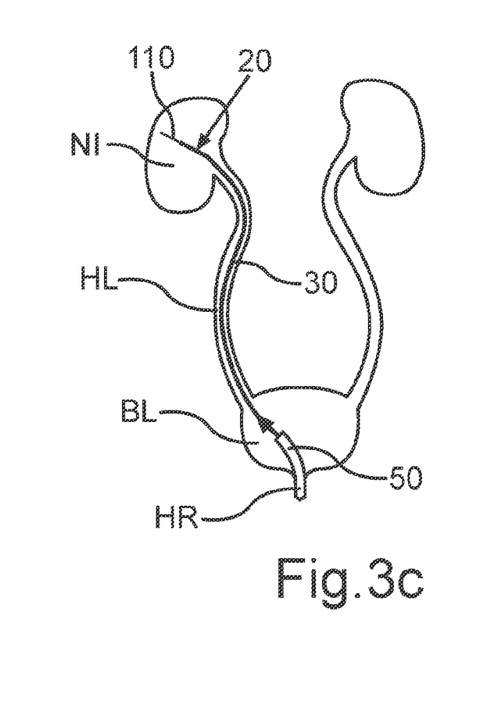

FIG. 3c shows how the ureteral stent 20 can be shifted along the guide element 110 through the bladder BL towards the left ureter HL in the drawing plane and thereby towards the left kidney NI in the drawing plane by means of the introduction component 50 subsequently thereto. In order to allow this, the guide element 110 is introduced into a main body passage opening 31 associated with the ureteral stent main body 30 on the one hand and into a receiving body passage opening 42 associated with the receiving body 40 on the other hand. In addition, the guide element 110 is passed through respective pipe passage openings 62, 72 of the introduction component 50, while the ureteral stent 20 is held on the introduction component 50.

Figure 3D:
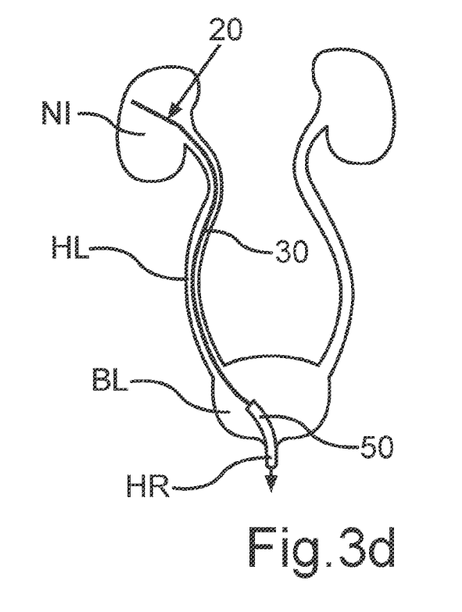
Figure 3E:
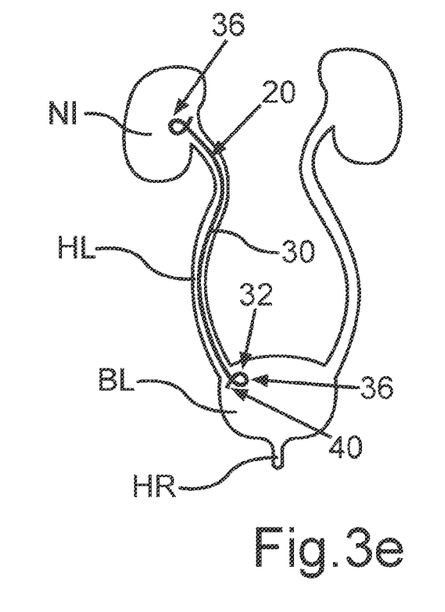

Based on FIG. 3d, it is apparent how the guide element 110 is removed as soon as the ureteral stent 20 is introduced into the (left) kidney NI in certain areas on the one hand and into the bladder BL in certain areas on the other hand. FIG. 3e finally shows a predetermined position of the ureteral stent 20 for the intended use thereof. For the intended use of the ureteral stent 20, main body ends of the ureteral stent main body 30 opposing each other are each j-shaped coiled in the respective basic position 36 thereof, whereby undesired slipping of the ureteral stent 20 within the urinary system can be avoided.

The ureteral stent 20 is translationally displaceable within the urinary system in directions of movement R1, R2 opposite to each other by means of the introduction component 50. The directions of movement R1, R2 opposite to each other are illustrated in FIG. 2 by straight arrows directed opposite to each other. In addition, the introduction component 50 is formed to guide the ureteral stent main body 30 and the receiving body 40 in the respective directions of movement R1, R2 in displacing along the guide element 110 and within the urinary system. Moreover, the ureteral stent main body 30 can be rotated together with the receiving body 40 in rotational directions D1, D2 opposite to each other in synchronous manner and in relation to the pliable guide element 110 based on the introduction component 50. The rotational directions D1, D2 are illustrated in FIG. 2 by bent arrows directed opposite to each other.

Based on FIG. 1 and FIG. 2, it is additionally apparent that the at least one connection element 22 (here: thread) is strained by means of the introduction component 50 with the ureteral stent 20 held on the introduction component 50.

Figure 4:
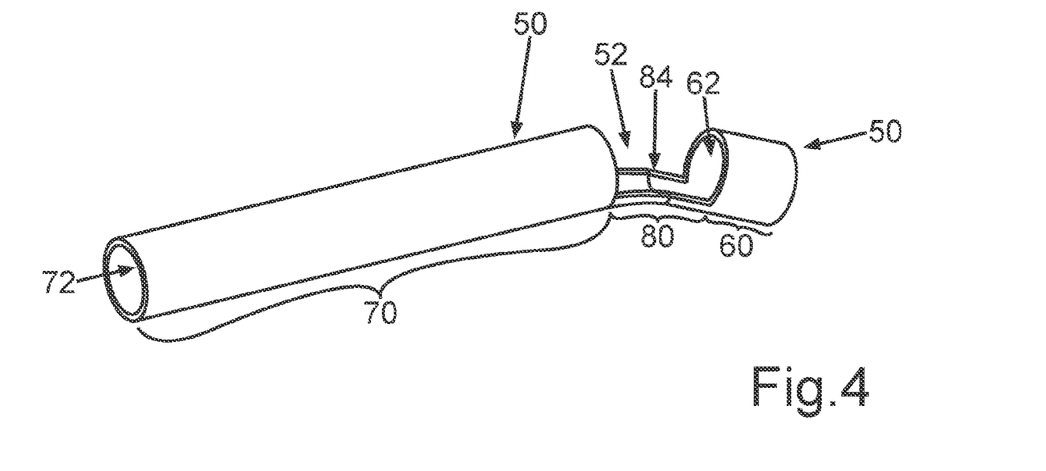
FIG. 4 a schematic perspective view of the introduction component, wherein a connection area of the introduction component is in a release position.
Figure 5:
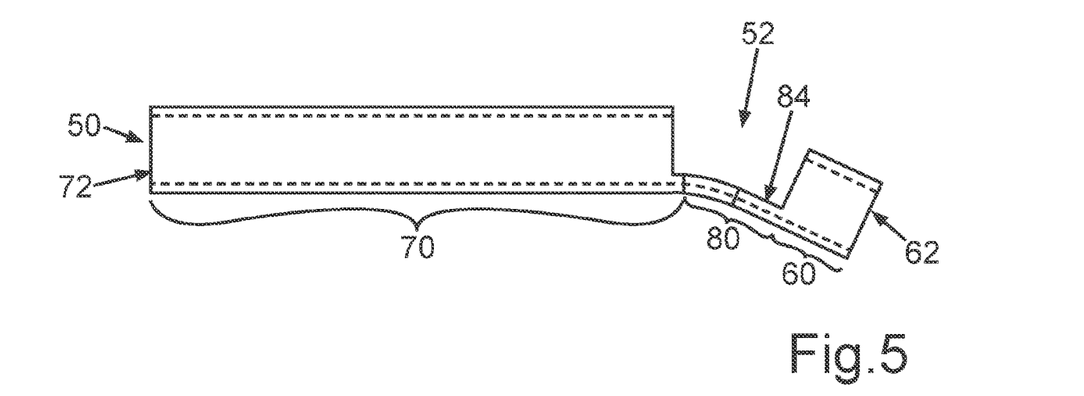
FIG. 5 a schematic side view of the introduction component.

By synopsis of FIG. 1, FIG. 4 and FIG. 5, it is particularly clearly apparent that the introduction component 50 comprises a recess 52 for introducing and holding the receiving body 40. Therein, the recess 52 serves as a receptacle for the receiving body 40. Presently, the introduction component 50 comprises two pipe sections, namely a first pipe section 60 and a second pipe section 70, into which the pliable guide element 110 can be introduced, as was already described in context of FIG. 3c. Furthermore, the introduction component 50 comprises a connection area 80, which connects the pipe sections 60, 70 to each other. The two pipe sections 60, 70 and the connection area 80 commonly delimit the recess 52 as is in particular apparent based on FIG. 4 and FIG. 5.

Figure 6:
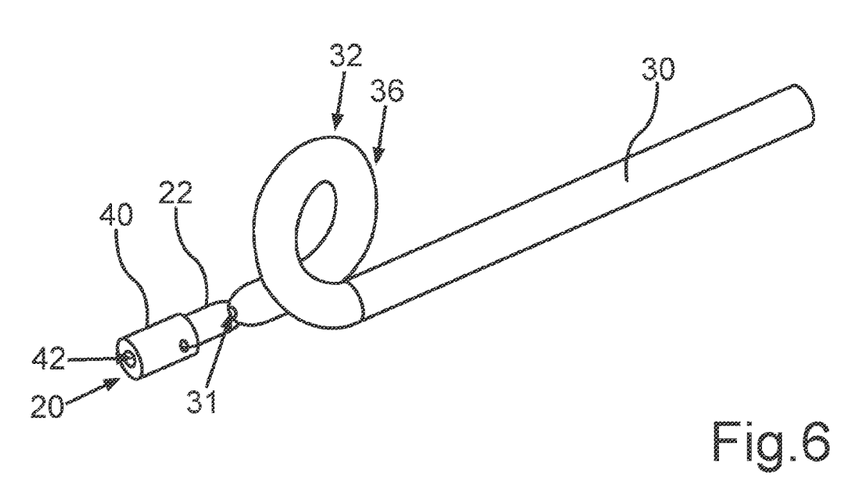
FIG. 6 a schematic perspective view of a distal main body end of a ureteral stent main body of the ureteral stent as well as of a receiving body of the ureteral stent, which is connected to the distal main body end via a connection element of the ureteral stent.
Figure 7:
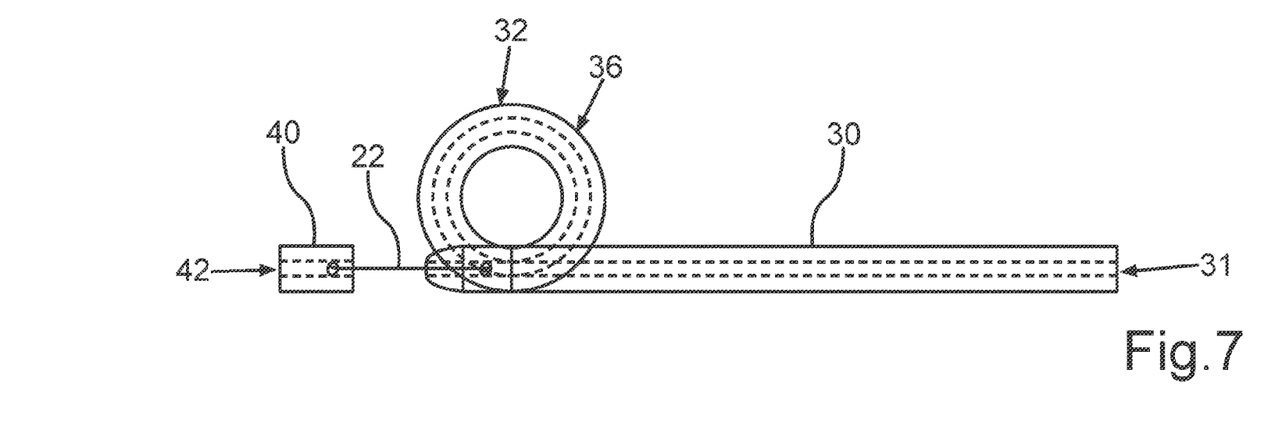
FIG. 7 a schematic side view of the distal main body end and of the receiving body connected to the distal main body end via the connection element.

Presently, the first pipe section 60 is formed as a proximal end of the introduction component 50, into which a distal main body end 32 of the ureteral stent main body 30 facing the receiving body 40 is introduced in certain areas—with the ureteral stent 20 held on the introduction component 50 (see FIG. 1). The guide element 110, which is passed both through the introduction component 50 and through the receiving body 40 and through the ureteral stent main body 30, keeps the distal main body end 32 introduced in certain areas strained, in particular stretched, in an introduction position 34. Moreover, the first pipe section 60, into which the distal main body end 32 is introduced, can also contribute to keep the distal main body end 32 strained. Thus, the first pipe section 60 can at least assist holding the distal main body end 32 in the introduction position 34—with the ureteral stent 20 held on the introduction component 50. The distal main body end 32 is formed to autonomously deform from the introduction position 34 into the basic position 36, which is apparent in FIG. 3e and particularly clearly in FIG. 6 and FIG. 7, of the distal main body end 32 and thereby to autonomously move out of the first pipe section 60. In the basic position 36 of the distal main body end 32, the latter one is relaxed compared to the introduction position 34. By synopsis of FIG. 2, in which the introduction position 34 of the distal main body end 32 is particularly clearly apparent, and FIG. 7, which shows the basic position 36 of the distal main body end 32, it is apparent that the distal main body end 32 is coiled in the basic position 36 thereof and in contrast to the introduction position 34 and thereby has a larger radial extension than in the introduction position 34. By the basic position 36, the undesired slipping of the ureteral stent main body 30 and thereby of the entire ureteral stent 20 within the urinary system is avoided.

The distal main body end 32 is formed, upon (autonomous) movement thereof out of the first pipe section 60 and by deforming from the introduction position 34 into the basic position 36, to extract the receiving body 40 from the recess 52 via the connection element 22. Hereto, the pliable guide element 110 can first be extracted at least from the first pipe section 60 and thereby out of the first pipe passage opening 62, whereby the distal main body end 32 elastically and thereby autonomously deforms from the introduction position 34 into the basic position 36 and thereby autonomously moves out of the first pipe section 60. During the deformation, the distal main body end 32 can support itself on the first pipe section 60 and extract the receiving body 40 from the recess 52 via the connection element 22. Thus, the distal main body end 32 is formed, upon guiding it out of the first pipe section 60 and by deforming from the introduction position 34 into the basic position 36, to extract the receiving body 40 from the recess 52 via the connection element 22.

In order to facilitate the extraction of the receiving body 40 from the recess 52, the connection area 80 is elastically deformable between a release position 84 shown in FIG. 4 and FIG. 5, in which the two pipe sections 60, 70 are tilted in relation to each other by means of the connection area 80 and thereby the recess 52 is expanded in certain areas for release of the extraction of the receiving body 40, and a holding position 86 shown in FIG. 1 and FIG. 2, in which the recess 52 is constricted compared to the release position 84 for holding the receiving body 40.

As long as the pliable guide element 110 (guide wire) is passed through the two pipe passage openings 62, 72 of the respective pipe sections 60, 70 of the introduction component 50 as well as through the main body passage opening 31 and the receiving body passage opening 42, the pliable guide element 110 prevents the elastic deformation of the connection area 80 from the holding position 86 thereof into the release position 84 thereof and in particular holds the connection area 80 pre-strained in the holding position 86. However, as soon as the pliable guide element 110 is completely extracted at least from the main body passage opening 31 and the first pipe passage opening 62, the pliable guide element 110 no longer counteracts the elastic deformation of the connection area 80 from the holding position 86 thereof into the release position 84 thereof, whereby the connection area 80 can autonomously elastically deform from the holding position 86 into the release position 84. By the tilt of the two pipe sections 60, 70 caused hereby, the recess 52 is expanded as is particularly clearly apparent in FIG. 4 and FIG. 5.

Thus, the connection area 80 is held pre-strained in the holding position 86 based on the guide element 110 with the ureteral stent 20 held by means of the introduction component 50 as well as with the guide element 110 introduced into the pipe sections 60, 70, wherein the elastic deformation of the connection area 80 from the holding position 86 thereof into the release position 84 thereof can be blocked by means of the introduced guide element 110 as long as the guide element 110 is in particular introduced into the first pipe passage opening 62 of the first pipe section 60 and into the main body passage opening 31 of the ureteral stent main body 30.

In summary, the introduction component 50 allows the movement of the ureteral stent 20 (thus of the ureteral stent main body 30 and of the receiving body 40, which is coupled to the ureteral stent main body 30 via the connection element 22), the rotational movements D1, D2 as well as the translational movements along the different directions of movement R1, R2 in relation to the pliable guide element 110 (guide wire). Thus, a positioning of the ureteral stent 20 is allowed by advancing and retracting as well as by rotation of the ureteral stent 20 upon insertion thereof into the urinary system.

The introduction component 50, which can also be referred to as introduction aid, thus serves for positioning the ureteral stent 20, wherein the introduction component 50 does not require additional mechanics and special movements are in particular not required to detach the ureteral stent 20 after the positioning thereof from the introduction component 50. Due to the special configuration of the introduction component 50, it is sufficient to extract the pliable guide element 110 from of the ureteral stent 20 and from of the introduction component 50 to thereby effect the detachment of the ureteral stent 20 from the introduction component 50.

The connection between the introduction component 50 (pusher) and the ureteral stent 20 can in particular be autonomously detached without movement especially provided thereto in extracting the pliable guide element 110.

The connection between the ureteral stent 20 and the introduction component 50 can in particular be detached by a resilient movement of the distal main body end 32 from the introduction position 34 thereof into the basic position 36 thereof as well as by a further resilient movement of the connection area 80 from the holding position 86 thereof into the release position 84 thereof, wherein the connection area 80 can be associated with the proximal end of the introduction component 50.

In introducing the pliable guide element 110, the connection area 80 first experiences a reversible shape change, wherein the connection area 80 is thereby strained and deformed from the release position 84 into the holding position 86. In the holding position 86, a better seat of the receiving body 40 in the recess 52 of the introduction component 50 is given than in the release position 84. The opposite deformation of the connection area 80 from the holding position 86 back into the release position 84 can be effected by extracting the pliable guide element 110 at least from the main body passage opening 31 and the first pipe passage opening 62. In the release position 84, compared to the holding position 86, a simplified removal of the receiving body 40 from the recess 52 (expanded in the release position 84 of the connection area 80) can be effected. The distal main body end 32 also experiences a reversible shape change from the basic position 36 into the introduction position 34 by introducing the pliable guide element 110 into the main body passage opening 31. The autonomous, opposite and thereby backward elastic deformation of the distal main body end 32 from the introduction position 34 into the basic position 36 is effected by extracting the guide element 110 at least from the main body passage opening 31. This backward elastic deformation from the introduction position 34 into the basic position 36 effects the extraction of the receiving body 40 via the connection element 22 based on the distal main body end 32.

Figure 8A:
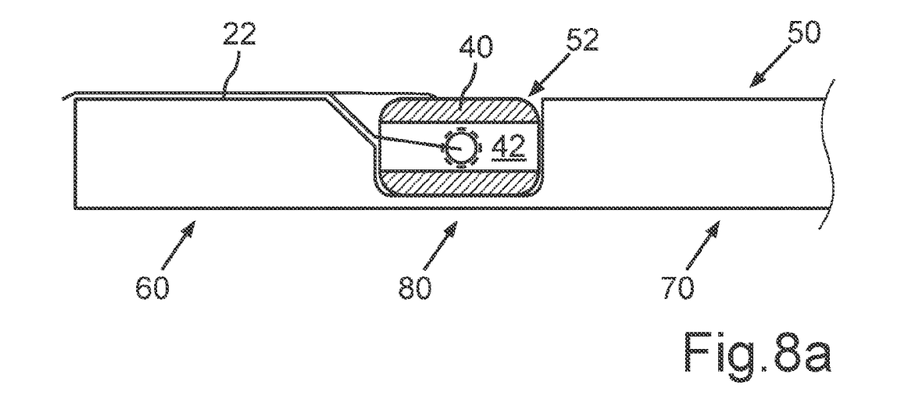
FIG. 8a-c schematic illustrations of various embodiments of the introduction component of the application device according to the invention.
Figure 8B:
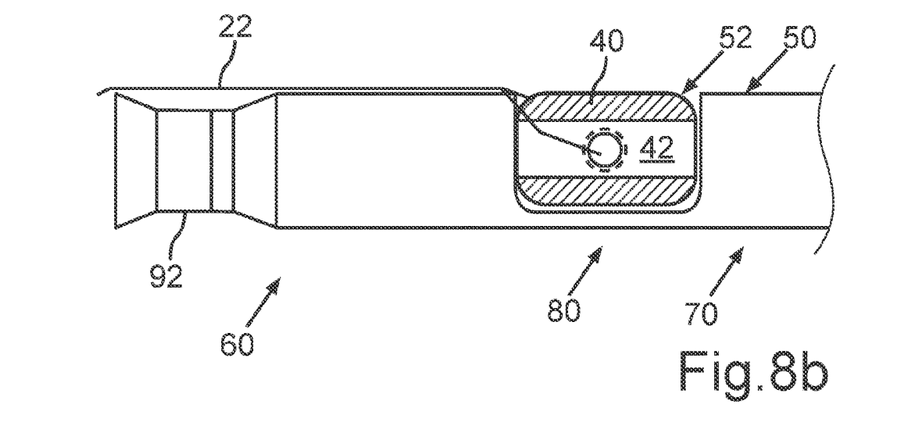
Figure 8C:
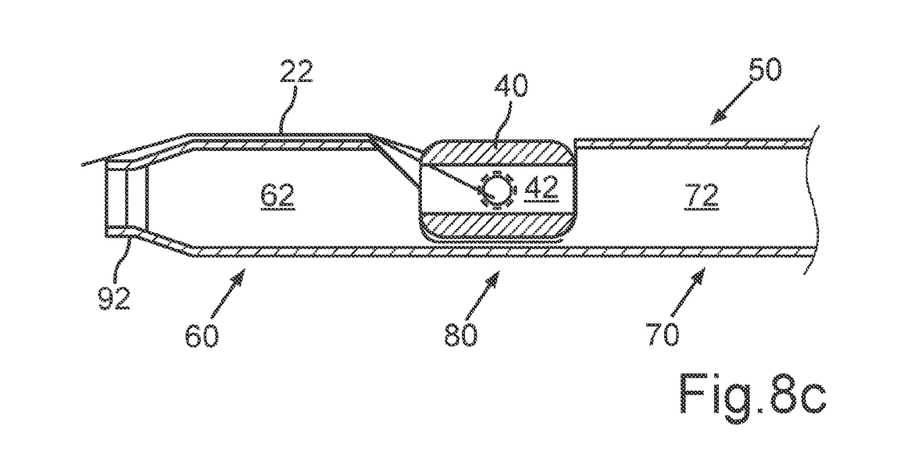

FIGS. 8a to 8c show schematic representations of various embodiments of the introduction component 50 of the application device 10. In FIG. 8a, an introduction component 50 with the receiving body 40 inserted into the recess 52 is illustrated. One recognizes that the recess 52 comprises an inclination 88 in the end area facing the first pipe section 60 such that a diameter of the recess 52 continuously increases towards the outside in the area of the inclination 88. The inclination 88 facilitates extraction of the receiving body 40 by means of the distal end 32 of the ureter main body 30 (not illustrated here) from the recess 52. Furthermore, one recognizes that the connection element 22 is formed thread-shaped and is arranged extending through a corresponding opening in the receiving body 40.

In FIG. 8b, a further embodiment of the introduction component 50 with the receiving body 40 inserted into the recess 52 is illustrated. One recognizes that the first, proximal pipe section 60 of the introduction component 50 comprises a constriction 92 in a proximal end area, wherein an internal diameter of the constriction 92 is smaller than an external diameter of the distal end 32 of the ureteral stent main body 30 (not illustrated here). Furthermore, one recognizes that the proximal end of the proximal pipe section 60 is formed funnel-shaped. In FIG. 8c, a further embodiment of the introduction component 50 with the receiving body 40 inserted in the recess 52 is illustrated. One recognizes that the first, proximal pipe section 60 of the introduction component 50 is here formed tapering in a proximal end area such that the internal diameter of the constriction 92 is smaller than the external diameter of the distal end 32 of the ureteral stent main body 30 (not illustrated here). These configurations allow that the distal end 32 of the ureteral stent main body 30 cannot or cannot excessively penetrate into the introduction component and thus difficulties in detaching the distal end 32 from the introduction component 50 optionally occur.

Figure 9A:
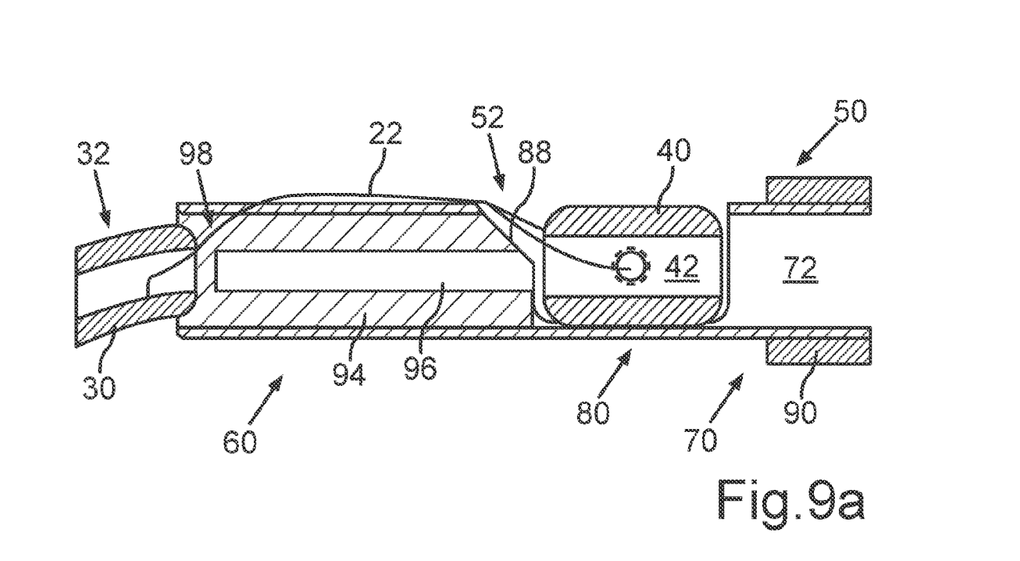
FIG. 9a-b schematic illustrations of further embodiments of the introduction component of the application device according to the invention.
Figure 9B:
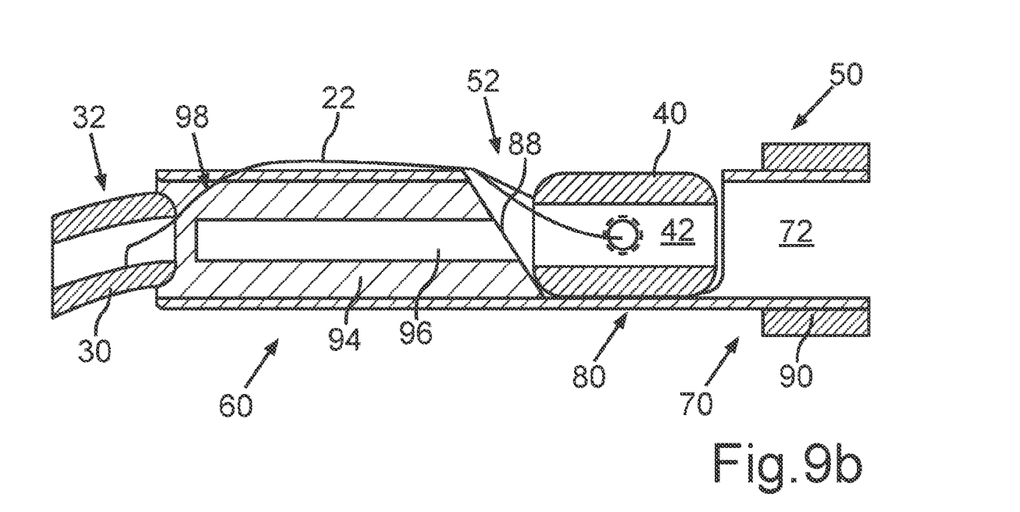

FIGS. 9a and 9b show schematic representations of further embodiments of the introduction component 50 of the application device 10. In FIG. 9a, an introduction component 50 with the receiving body 40 inserted in the recess 52 is illustrated. One recognizes that according to this embodiment, a tube 94 is arranged in the first, proximal pipe section 60 of the introduction component 50, wherein the tube 94 comprises a tube passage opening 96, the diameter of which is approximately equal to or equal to a diameter of the passage opening 42 of the receiving body 40. In addition, the tube 94 comprises an inclination 88 at its distal end, which results in an expansion of the diameter of the recess 52. Therein, the inclination 88 extends at a 45° angle over a length of approximately half of the diameter of the tube 94. The proximal end of the tube 94 is formed funnel-shaped for receiving the distal end 32 of the ureteral main body 32. Furthermore, one recognizes that it comprises a notch 98 for introducing and holding the thread-shaped connection element 22, in particular for receiving the two ends of the thread-shaped connection element 22, in the proximal end area of the proximal pipe section 60.

The two ends of the thread-shaped connection element 22 are attached to the distal end 32 of the ureteral main body 32. The application device 10 according to this embodiment additionally comprises a mounting sleeve 90, wherein the mounting sleeve 90 is formed such that an internal diameter of the mounting sleeve 90 is equal to or larger than an external diameter of the introduction component 50. The mounting sleeve 90 serves for fixing the receiving body 40 in the recess 52 of the introduction component 50 before passing the guide element 110 (not illustrated here) through the corresponding passage openings 72, 96, 42 of the introduction component 50, of the tube 94 and of the receiving body 40. Thus, the receiving body 40 can be securely held and fixed in the recess 52, respectively.

The embodiment of the introduction component 50 illustrated in FIG. 9b corresponds to the embodiment described and illustrated in FIG. 9a. In contrast to the previously described introduction component, the inclination 88 formed in the distal area of the tube 94 extends over the entire diameter of the tube 94. The inclination 88 again serves for expanding the diameter of the recess 52 in radial direction to the outside. Furthermore, one recognizes that in the introduction components 50 illustrated in FIGS. 9a and 9b, the proximal end is additionally formed rounded. This configuration results in an advantageous atraumatic tip design of the introduction component 50.

The invention claimed is:

1. An application device comprising:
 a ureteral stent, which comprises a ureteral stent main body and a receiving body connected to the ureteral stent main body by at least one elongated connection element of the ureteral stent,
 a pliable guide element on which the ureteral stent is positioned, and
 an introduction component configured for holding the ureteral stent and guiding the ureteral stent through a ureter of a patient along the pliable guide element,
 wherein the ureteral stent is displaceable along the pliable guide element in directions of movement opposite to each other by displacing the introduction component, and the introduction component is formed to guide the ureteral stent main body and the receiving body in displacing in the respective directions of movement,
 wherein the introduction component comprises a recess for introducing and holding the receiving body,
 wherein the introduction component comprises at least two pipe sections, into which the pliable guide element can be introduced, as well as at least one connection area connecting the at least two pipe sections to each other, wherein the at least two pipe sections and the at least one connection area delimit the recess, and
 wherein a first pipe section of the at least two pipe sections is formed as a proximal end of the introduction component, into which a distal main body end of the ureteral stent main body facing the receiving body is introduced at least in certain areas at least with the ureteral stent held on the introduction component.

2. The application device according to claim 1, wherein the receiving body has ferromagnetic characteristics.

3. The application device according to claim 1, wherein the ureteral stent main body is rotatable together with the receiving body in relation to the pliable guide element based on the introduction component.

4. The application device according to claim 1, wherein the at least one elongated connection element is non-rigidly or pliably formed.

5. The application device according to claim 1, wherein the at least one elongated connection element is strained by means of the introduction component with the ureteral stent held on the introduction component.

6. The application device according to claim 4, wherein the at least one elongated connection element is formed as a thread element or wire element.

7. The application device according to claim 1, wherein the distal main body end introduced at least in certain areas can be held in an introduction position on the first pipe section by means of the guide element with the ureteral stent held on the introduction component, wherein the distal main body end is formed to autonomously deform from the introduction position into a basic position of the distal main body end with the guide element detached from the ureteral stent main body and to thereby move out of the first pipe section.

8. The application device according to claim 1, wherein the distal main body end is formed, upon movement thereof out of the first pipe section and by deformation from the introduction position into the basic position, to extract the receiving body from the recess via the at least one elongated connection element.

9. The application device according to claim 1, wherein the first, proximal pipe section of the introduction component comprises a constriction in a proximal end area, wherein an internal diameter of the constriction is smaller than an external diameter of the distal end of the ureteral stent main body or that the first, proximal pipe section of the introduction component is formed tapering in a proximal end area such that the internal diameter of the constriction is smaller than the external diameter of the distal end of the ureteral stent main body.

10. The application device according to claim 1, wherein the first, proximal pipe section of the introduction component comprises a first pipe passage opening, the diameter of which decreases towards the receiving body such that it is approximately equal to or equal to a diameter of a passage opening of the receiving body.

11. The application device according to claim 1, wherein a tube is arranged in the first, proximal pipe section of the introduction component, wherein the tube comprises a tube passage opening, the diameter of which decreases towards the receiving body such that it is approximately equal to or equal to a diameter of a passage opening of the receiving body, or the tube comprises a tube passage opening, the diameter of which is approximately equal to or equal to a diameter of a passage opening of the receiving body.

12. The application device according to claim 1, wherein the recess comprises at least one inclination and/or at least one step in the end area facing the first pipe section such that a diameter of the recess increases in the area of the inclination or step.

13. The application device according to claim 1, wherein at least one notch or peripheral recess for receiving and guiding the elongated connection element is formed in a proximal end area of the first, proximal pipe section of the introduction component.

14. The application device according to claim 1, wherein a proximal end area of the first, proximal pipe section of the introduction component is formed funnel-shaped for receiving the distal main body end.

15. The application device according to claim 11, wherein a proximal end area of the tube is formed funnel-shaped for receiving the distal main body end and/or a distal end area of the tube comprises at least one inclination and/or at least one step such that a diameter of the recess increases in the area of the inclination or step.

16. The application device according to claim 1, wherein the at least one connection area is deformable between a release position, in which the at least two pipe sections are tilted in relation to each other by means of the at least one connection area and thereby the recess is expanded at least in certain areas for releasing the receiving body, and a holding position, in which the recess is constricted compared to the release position for holding the receiving body.

17. The application device according to claim 16, wherein the at least one connection area can be held in the holding position based on the guide element with the ureteral stent held by means of the introduction component as well as with the guide element introduced into the at least two pipe sections, wherein an elastic deformation of the at least one connection area from the holding position thereof into the release position thereof can be blocked by means of the introduced guide element.

18. The application device according to claim 1, wherein the elongated connection element is at least partially guided on an outer surface of the proximal end of the introduction component with the ureteral stent held on the introduction component.

19. The application device according to claim 1, wherein the application device comprises a mounting sleeve, wherein the mounting sleeve is formed such that an internal diameter of the mounting sleeve is equal to or larger than an external diameter of the introduction component.

* * * * *